(12) United States Patent
Rieping

(10) Patent No.: US 7,759,094 B2
(45) Date of Patent: Jul. 20, 2010

(54) METHOD FOR THE PRODUCTION OF L-AMINO ACIDS USING STRAINS FROM THE ENTEROBACTERIACEAE FAMILY WHICH CONTAIN AN ENHANCED LAMB GENE

(75) Inventor: Mechthild Rieping, Bielefeld (DE)

(73) Assignee: Degussa GmbH, Dusseldorf (DE)

( * ) Notice: Subject to any disclaimer, the term of this patent is extended or adjusted under 35 U.S.C. 154(b) by 529 days.

(21) Appl. No.: 11/658,477

(22) PCT Filed: Jul. 5, 2005

(86) PCT No.: PCT/EP2005/007212

§ 371 (c)(1),
(2), (4) Date: Jan. 25, 2007

(87) PCT Pub. No.: WO2006/015669

PCT Pub. Date: Feb. 16, 2006

(65) Prior Publication Data

US 2009/0068711 A1    Mar. 12, 2009

(30) Foreign Application Priority Data

Aug. 3, 2004  (DE) ................ 10 2004 037 572

(51) Int. Cl.
*C12P 13/04* (2006.01)
*C12P 13/08* (2006.01)
*C12P 21/02* (2006.01)
*C07K 14/195* (2006.01)

(52) U.S. Cl. ............ 435/106; 435/115; 435/69.1; 530/350; 530/825

(58) Field of Classification Search ............... 435/106, 435/115, 69.1; 530/350, 825
See application file for complete search history.

(56) References Cited

U.S. PATENT DOCUMENTS 4,278,765 A    7/1981    Debabov et al.

(Continued)

FOREIGN PATENT DOCUMENTS

DE    101 02 823    11/2001

(Continued)

OTHER PUBLICATIONS

Current Protocols in Molecular Biology, Hybridization Analysis of DNA Blots, Meinkoth and Wahl equation, pp. 2.10.8-2.10.11, 1993.*

(Continued)

*Primary Examiner*—Karen Cochrane Carlson
*Assistant Examiner*—Rosanne Kosson
(74) *Attorney, Agent, or Firm*—Law Office of: Michael A. Sanzo, LLC

(57) ABSTRACT

The invention relates to a method for the production of L-amino acids by fermentation of recombinant microorganisms of the Enterobacteriaceae family, characterized in that a) the microorganisms producing the desired L-amino acid and wherein the lamB-gene or nucleotide sequence coding for the gene product maltoporin is amplified, particularly overexpressed, are cultivated in a medium in conditions enabling the desired L-amino acid to be enriched in the medium or in cells, and b) the desired L-amino acid is isolated, wherein constituents of the fermentation broth and/or biomass remain in the entirety thereof or in parts thereof (=0 bis 100%) in the isolated product or are fully removed.

19 Claims, 2 Drawing Sheets

Map of the plasmid pTrc99AlamB

U.S. PATENT DOCUMENTS

| | | | |
|---|---|---|---|
| 6,362,002 | B1 * | 3/2002 | Denison et al. ............... 436/2 |
| 2002/0155551 | A1 | 10/2002 | Rieping |

FOREIGN PATENT DOCUMENTS

| | | |
|---|---|---|
| EP | 1 382 685 | 1/2004 |
| WO | WO-03/004670 | 1/2003 |
| WO | WO-03/008605 | 1/2003 |
| WO | WO-03/076635 | 9/2003 |

OTHER PUBLICATIONS

Sousa et al., "The ARO4 gene of *Candida albicans* encodes a tyrosine-sensitive DAHP synthase: evolution, functional conservation and phenotype of Aro3p-, Aro4p-deficient mutants," Microbiology 148(Pt5):1291-1303, 2002.*

Clément, et al., "Gene Sequence of the λ Receptor, an Outer Membrane Protein of *E. coli* K12," *Cell*, vol. 27, 504-514 (Dec. 1981).

Francoz, et al., "The Maltoporin of *Salmonella typhimurium*: Sequence and Folding Model," *Res. Microbiol.*, 141, 1039-1059 (1990).

Ghosh, et al., "Overexpression of Outer Membrane Porins in *E. coli* Using pBluescript-Derived Vectors," *Gene Expression*, vol. 7, 149-161 (1998).

Kruse, et al., "Influence of Threonine Exporters on Threonine Production in *Escherichia coli*," *Appl. Microbiol. Biotechnol.*, 59:205-210 (2002).

Newton, et al., "Studies of the Anaerobically Induced Promoter pnirB and the Improved Expression of Bacterial Antigens," *Res. Microbiol.*, 146, 193-202 (1995).

Wei, et al., "Complete Genome Sequence and Comparative Genomics of *Shigella flexneri* Serotype 2a Strain 2457T," *Infection and Immunity*, vol. 71, No. 5:2775-2786 (May 2003).

International Search Report for PCT/EP2005/007212, 2006.

English language translation of the International Search Report for PCT/EP2005/007212 filed Jul. 5, 2005.

English language translation of the Written Opinion of the International Searching Authority for PCT/EP2005/007212 filed Jul. 5, 2005.

English language translation of the International Preliminary Report on Patentability for PCT/EP2005/007212 filed Jul. 5, 2005.

* cited by examiner

Figure 1: Map of the plasmid pTrc99AlamB
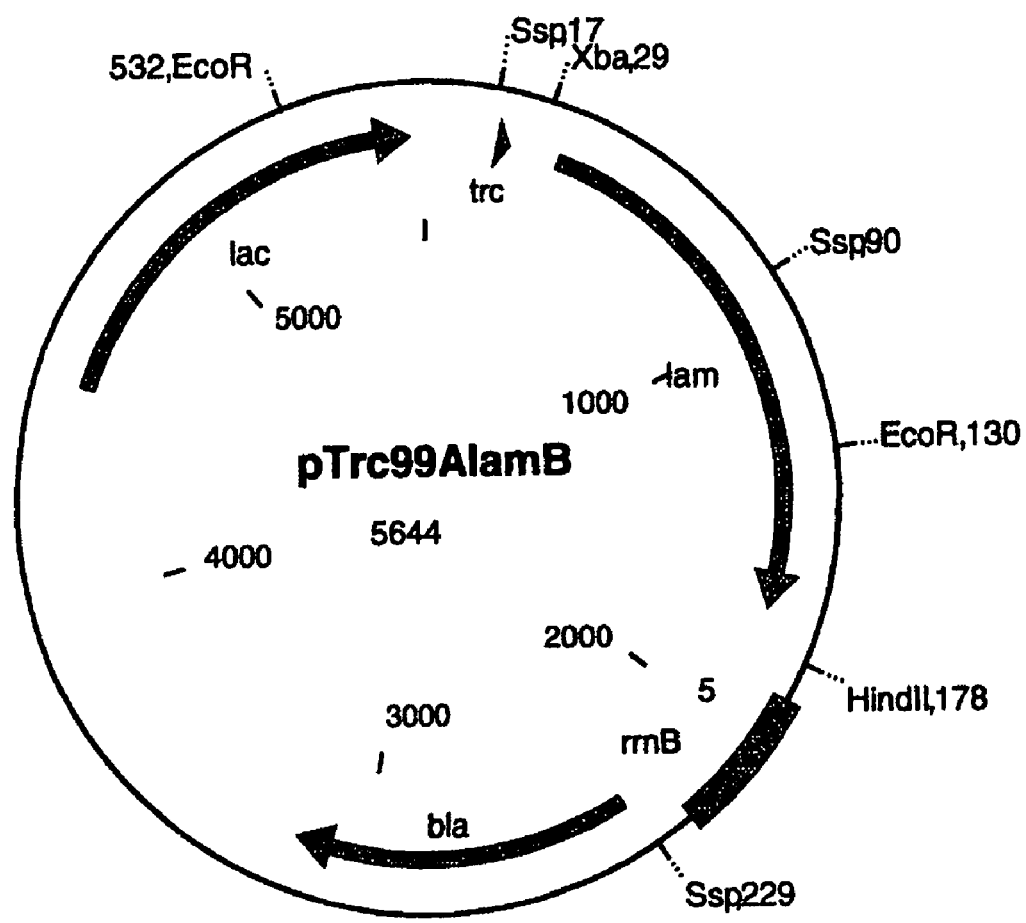

Figure 2: Map of the plasmid pMW218lamB
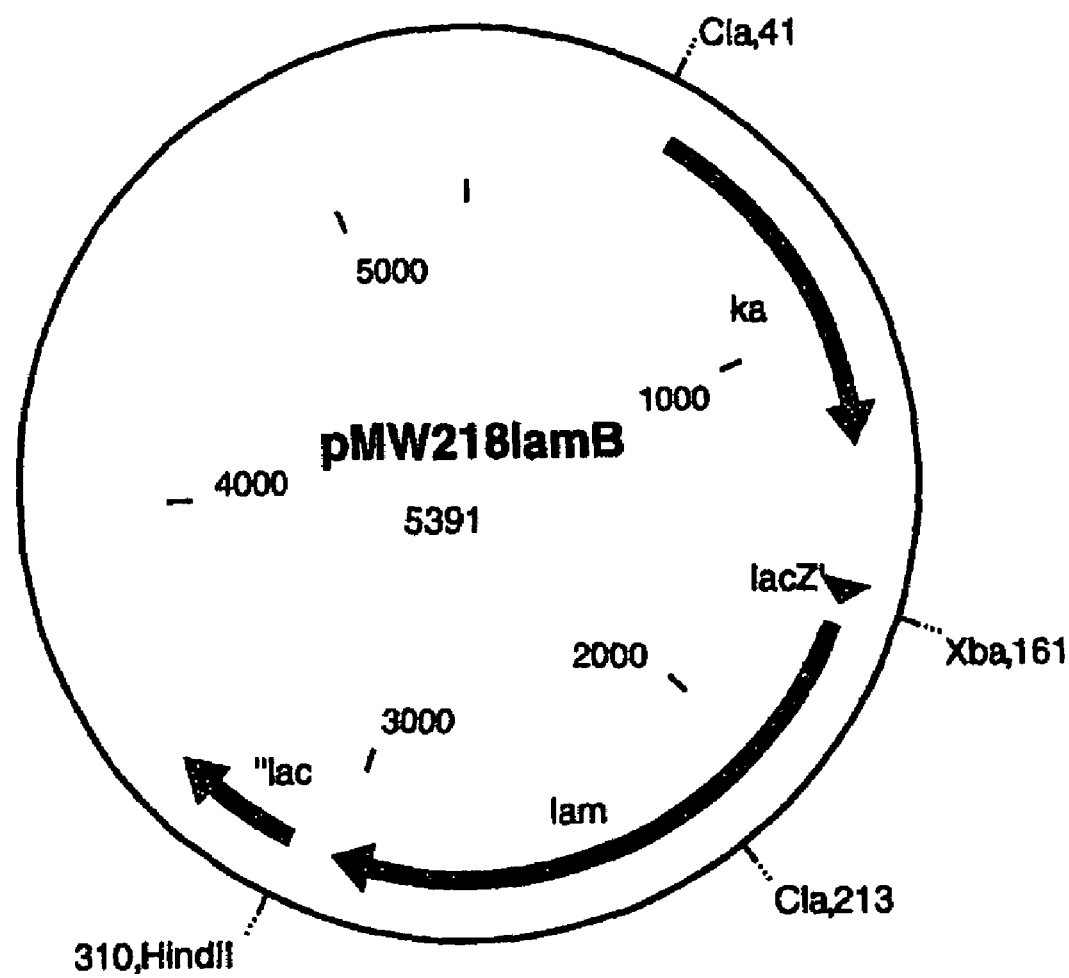

METHOD FOR THE PRODUCTION OF L-AMINO ACIDS USING STRAINS FROM THE ENTEROBACTERIACEAE FAMILY WHICH CONTAIN AN ENHANCED LAMB GENE

CROSS REFERENCE TO RELATED APPLICATIONS

This application is the U.S. national phase of International Application No. PCT/EP05/07212, filed on Jul. 5, 2005, which claims priority to German Application No. 10 2004 037 572.0, filed on Aug. 3, 2004.

This invention relates to a method for the production of L-amino acids, in particular L-threonine, using recombinant microorganisms of the family Enterobacteriaceae, in which the lamB gene or nucleotide sequences coding for its gene product maltoporin is or are amplified, in particular overexpressed, and these microorganisms.

BACKGROUND OF THE INVENTION

L-Amino acids, in particular L-threonine, are used in human medicine and in the pharmaceutical industry, in the food industry and very particularly in animal nutrition.

It is known that L-amino acids are produced by fermentation of strains of the Enterobacteriaceae, in particular *Escherichia coli* (*E. coli*) and *Serratia marcescens*. Because of the great importance, work is, continuously being carried out on the improvement of the production methods. Method improvements can relate to fermentation measures, such as, for example, agitation and supply with oxygen, or the composition of the nutrient media, such as, for example, the sugar concentration during the fermentation, or the workup to give the product form, by, for example, ion-exchange chromatography, or the intrinsic performance properties of the microorganism itself.

To improve the performance properties of these microorganisms, methods of mutagenesis, selection and mutant selection are employed. In this manner strains are obtained which are resistant to antimetabolites such as, for example, the threonine analog α-amino-β-hydroxyvaleric acid (AHV) or are auxotrophic for metabolites of importance in regulation and produce L-amino acids such as, for example L-threonine.

For some years, likewise methods of recombinant DNA technology have been used for strain improvement of L-amino acid-producing strains of the family Enterobacteriaceae, by amplifying individual amino acid biosynthesis genes and studying the effect on production. Summarizing information on cell and molecular biology of *Escherichia coli* and *Salmonella* is to be found in Neidhardt (ed): *Escherichia coli* and *Salmonella*, Cellular and Molecular Biology, 2nd edition, ASM Press, Washington, D.C., USA, (1996).

SUMMARY OF THE INVENTION

The object of the invention for the inventors was to provide novel measures for the improved production by fermentation of L-amino acids, in particular L-threonine.

DETAILED DESCRIPTION OF THE INVENTION

The invention relates to recombinant microorganisms of the family Enterobacteriaceae which contain an amplified or overexpressed lamB gene which codes for a polypeptide having the activity of the maltoporin LamB and which produce, in an improved manner, L-amino acids, in particular L-threonine.

As starting point for the comparison there serve in each case the non-recombinant microorganisms which do not contain an amplified lamB gene.

These microorganisms comprise, in particular, microorganisms of the family Enterobacteriaceae in which a polynucleotide is amplified which codes for a polypeptide which is up to at least 90%, in particular identical at least 95%, preferably 99%, to an amino acid sequence selected from the group SEQ ID No. 4, SEQ ID No. 6, and SEQ ID No. 8, the polypeptide having the activity of the maltoporin LamB.

Preference is given to amino acid sequences which are identical to those of SEQ ID No. 4, SEQ ID No. 6 or SEQ ID No. 8.

Said microorganisms contain amplified or overexpressed polynucleotides, selected from the group:

a) polynucleotide having the nucleotide sequence SEQ ID No. 3, SEQ ID No. 5 or SEQ ID No. 7;
b) polynucleotide having a nucleotide sequence which corresponds to that of SEQ ID No. 3, SEQ ID No. 5 or SEQ ID No. 7 within the bounds of the degeneracy of the genetic code;
c) polynucleotide having a sequence which hybridizes under stringent conditions with the sequence complementary to the sequence SEQ ID No. 3, SEQ ID No. 5 or SEQ ID No. 7;
d) polynucleotide having a sequence SEQ ID No. 3, SEQ ID No. 5 or SEQ ID No. 7 which contains functionally neutral sense mutants, the polynucleotides coding for the gene product maltoporin (see below).

The invention likewise relates to a method for the production by fermentation of L-amino acids, in particular L-threonine, using recombinant microorganisms of the family Enterobacteriaceae which in particular already produce L-amino acids and in which at least the lamB gene or nucleotide sequences coding for its gene product maltoporin LamB is or are amplified.

Preferably, use is made of the described microorganisms.

If in the following L-amino acids or amino acids are mentioned, this means one or more amino acids including salts thereof selected from the group L-asparagine, L-threonine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine and L-homoserine. Particular preference is given to L-threonine.

The term "amplification" in this context describes the increase of the intracellular activity or concentration of one or more enzymes or proteins in a microorganism which are coded for by the corresponding DNA, for example, increasing the number of copies of the gene or genes by at least one (1) copy, functionally linking a strong promoter to the gene or using a gene or allele which codes for one corresponding enzyme or protein having a high activity and if appropriate combining these measures.

The amplification measures, in particular overexpression, increase the activity or concentration of the corresponding protein generally by at least 10%, 25%, 50%, 75%, 100%, 150%, 200%, 300%, 400% or 500%, at most up to 1000% or 2000% based on that of the wild type protein or on the activity or concentration of the protein in the non-recombinant microorganism. Non-recombinant microorganism or parent strain is taken to mean the microorganism on which the measures according to the invention are carried out.

The invention relates to a method for the production of L-amino acids by fermentation of recombinant microorganisms of the family Enterobacteriaceae, characterized in that
a) the microorganisms producing the desired L-amino acid in which the lamB gene or nucleotide sequence coding for its gene product is amplified, in particular overexpressed, are cultured in a medium under conditions in which the desired L-amino acid is enriched in the medium or in the cells and
b) the desired L-amino acid is isolated, if appropriate components of the fermentation broth and/or the biomass in its totality or fractions ($\geqq 0$ to 100%) remaining in the isolated product or being completely removed.

The in particular recombinant microorganisms having an amplified or overexpressed lamB gene, which are likewise subject matter of the present invention, can produce L-amino acids from glucose, sucrose, lactose, fructose, maltose, molasses, if appropriate starch, if appropriate cellulose, or from glycerol and ethanol. The microorganisms are members of the family Enterobacteriaceae selected from the genera *Escherichia, Erwinia, Providencia* and *Serratia*. The genera *Escherichia* and *Serratia* are preferred. In the case of the genus *Escherichia*, in particular mention may be made of the species *Escherichia coli*, and in the case of the genus *Serratia*, mention may be made, in particular, of the species *Serratia marcescens*.

Recombinant microorganisms are generally generated by transformation, transduction, conjugation or a combination of these methods using a vector which comprises the desired gene, an allele of this gene or parts thereof or a promoter amplifying the expression of the gene.

Suitable, in particular L-threonine-producing strains of the genus *Escherichia*, in particular of the species *Escherichia coli*, are, for example

*Escherichia coli*, H4581 (EP 0 301 572)
*Escherichia coli* KY10935 (Bioscience Biotechnology and Biochemistry 61(11): 1877-1882 (1997))
*Escherichia coli* VNIIgenetika MG442 (U.S. Pat. No. 4,278,765)
*Escherichia coli* VNIIgenetika M1 (U.S. Pat. No. 4,321,325)
*Escherichia coli* VNIIgenetika 472T23 (U.S. Pat. No. 5,631,157)
*Escherichia coli* BKIIM B-3996 (U.S. Pat. No. 5,175,107)
*Escherichia coli* kat 13 (WO 98/04715)
*Escherichia coli* KCCM-10132 (WO 00/09660)

Suitable L-threonine-producing strains of the genus *Serratia*, in particular the species *Serratia marcescens*, are, for example

*Serratia marcescens* HNr21 (Applied and Environmental Microbiology 38(6): 1045-1051 (1979))
*Serratia marcescens* TLr156 (Gene 57(2-3): 151-158 (1987))
*Serratia marcescens* T-2000 (Applied Biochemistry and Biotechnology 37(3): 255-265 (1992))

L-Threonine-producing strains of the Enterobacteriaceae family preferably possess, inter alia, one or more of the genetic or phenotypic features selected from the group: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidine, resistance to cyclopentanecarboxylic acid, resistance to rifampicin, resistance to valine analogs such as, for example, valine hydroxamate, resistance to purine analogs such as, for example, 6-dimethylaminopurine, requirement for L-methionine, if appropriate partial and compensatable requirement for L-isoleucine, requirement for meso-diaminopimelic acid, auxotrophy with respect to threonine-comprising dipeptides, resistance to L-threonine, resistance to threonine raffinate, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, if appropriate ability for sucrose utilization, amplification of the threonine operon, amplification of homoserine dehydrogenase I, aspartate kinase I prefers the feedback-resistant form, amplification of homoserine kinase, amplification of threonine synthase, amplification of aspartate kinase, if appropriate of the feedback-resistant form, amplification of aspartate semialdehyde dehydrogenase, amplification of phosphoenolpyruvate carboxylase, if appropriate of the feedback-resistant form, amplification of phosphoenolpyruvate synthase, amplification of transhydrogenase, amplification of the RhtB gene product, amplification of the RhtC gene product, amplification of the YfiK gene product, amplification of a pyruvate carboxylase, and attenuation of acetic acid formation.

It has been found that microorganisms of the family Enterobacteriaceae, after amplification, in particular overexpression of the lamB gene, produce, in an improved manner, L-amino acids, in particular L-threonine.

The nucleotide sequences of the genes or open reading frames (ORF) of *Escherichia coli* are part of the prior art and can be taken from the genome sequence of *Escherichia coli* published by Blattner et al. (Science 277: 1453-1462 (1997)). It is known that the N-terminal amino acid methionine can be eliminated by host-specific enzymes (methionine aminopeptidase).

The nucleotide sequences for the lamB gene are likewise known from *Shigella flexneri* and *Salmonella typhimirium* likewise part of the family Enterobacteriaceae.

The lamB gene of *Escherichia coli* is described, inter alia, by the following details:

Description: The lamB gene from *Escherichia coli* codes for the maltoporin LamB, which is also called maltose/maltodextrin-specific pore-forming membrane protein (porin).

Function: The maltoporin LamB from *Escherichia coli* is a trimeric protein which facilitates or enables the diffusion of maltose and maltodextrins through the external membrane of enteric bacteria and in addition acts as a non-specific porin for small hydrophilic molecules such as, for example, glucose or trehalose, and also as cell-surface receptor for phages.

Reference: Blattner et al.; Science 277 (5331): 1453-1474 (1997),
Clément et al.; Cell 27: 507-514 (1981),
Schwartz; Method of Enzymology 97: 100-112 (1983),
Death et al.; Journal of Bacteriology 175: 1475-1483 (1993),
Klein et al.; Journal of Microbiology 175: 1682-1686 (1993),
Szmelcman et al.; Journal of Bacteriology 124: 112-118 (1975),
Benz et al.; Biochem. Biophys. Acta 1104: 299-307 (1992)

Accession No.: AE000477

Alternative gene name: b4036

The nucleic acid sequences can be taken from the databases of the National Center for Biotechnology Information (NCBI) of the National Library of Medicine (Bethesda, Md., USA), the Nucleotide Sequence Database of the European Molecular Biologies Laboratories (EMBL, Heidelberg, Germany or Cambridge, UK) or the DNA Database of Japan (DDBJ, Mishima, Japan).

The nucleotide sequence of the lamB gene of *Escherichia coli* is found in the SEQ ID No. 3 and the known sequences for the lamB gene of *Shigella flexneri* (AE015426) and *Salmonella typhimurium* (AE008897) under the SEQ ID No. 5 and SEQ ID No. 7, respectively. The amino acid sequences of the proteins coded by these reading frames are given as SEQ ID No. 4, SEQ ID No. 6 and SEQ ID No. 8.

The genes described in the stated text passages can be used according to the invention. In addition, use can be made of alleles of the genes which result from the degeneracy of the genetic code or by functionally neutral sense mutations. The use of endogenous genes is preferred.

"Endogenous genes" or "endogenous nucleotide sequences" is taken to mean the genes or alleles or nucleotide sequences, respectively, present in the population of a species.

The suitable alleles of the lamB gene which comprise functionally neutral sense mutations contain, inter alia, those which lead to at least one (1) conservative amino acid replacement in the protein coded by them.

In the case of the aromatic amino acids, conservative replacements are when phenylalanine, tryptophan and tyrosine are exchanged for one another. In the case of the hydrophobic amino acids, conservative replacements are when leucine, isoleucine and valine are exchanged for one another. In the case of the polar amino acids, conservative replacements are when glutamine and asparagine are exchanged for one another. In the case of the basic amino acids, conservative replacements are when arginine, lysine and histidine are exchanged for one another. In the case of the acidic amino acids, conservative replacements are when aspartic acid and glutamic acid are exchanged for one another. In the case of the hydroxyl-containing amino acids, conservative replacements are when serine and threonine are exchanged for one another.

In the same manner, use can also be made of those nucleotide sequences which code for variants of the abovementioned proteins which in addition comprise at the N- or C-terminus an extension or shortening by at least one (1) amino acid. This extension or shortening is no more than 50, 40, 30, 20, 10, 5, 3 or 2 amino acids or amino acid residues.

The suitable alleles also comprise those which code for proteins in which at least one (1) amino acid is inserted or deleted. The maximum number of such modifications termed indels can be 2, 3, 5, 10, 20, but in no case more than 30 amino acids.

The suitable alleles comprise, in addition, those which are obtainable by hybridization, in particular under stringent conditions using SEQ ID No. 3, SEQ ID No. 5 or SEQ ID No. 7 or parts thereof in particular the coding regions or the sequences complementary thereto.

Those skilled in the art will find instructions on identifying DNA sequences by hybridization, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place under stringent conditions, that is hybrids are only formed where the probe and target sequence, that is the polynucleotides treated by the probe are at least 70% identical. It is known that the stringency of hybridization including the wash steps is influenced or determined by varying the buffer composition, the temperature and the salt concentration. The hybridization reaction is generally carried out at relatively low stringency compared with the wash steps (Hybaid Hybridisation Guide, Hybaid Limited, Teddington, UK, 1996).

For the hybridization reaction, use can be made of, for example, a buffer corresponding to 5×SSC buffer at a temperature of approximately 50° C.-68° C. In this case probes can also hybridize with polynucleotides which have less than 70% identity to the sequence of the probe. Such hybrids are less stable and are removed by washing under stringent conditions. This can be achieved, for example, by reducing the salt concentration to 2×SSC and if appropriate subsequently 0.5×SSC (The DIG System User's Guide for Filter Hybridisation, Boehringer Mannheim, Mannheim, Germany, 1995) a temperature of approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. being set. It is if appropriate possible to reduce the salt concentration to a concentration equivalent to 0.2×SSC or 0.1×SSC. By stepwise increase of the hybridization temperature in steps of approximately 1-2° C. from 50° C. to 68° C., polynucleotide fragments are isolated which have, for example, at least 70% or at least 80% or at least 90%, at least 91%, at least 92%, at least 93%, at least 94%, at least 95%, at least 96%, at least 97%, at least 98% or at least 99% identity to the sequence of the probe used. Further instructions on hybridization are available in the form of kits on the market (for example DIG Easy Hyb from Roche Diagnostics GmbH, Mannheim, Germany, Catalog No. 1603558). The resultant nucleotide sequences code for polypeptides which have at least 90% identity to the amino acid sequences given in SEQ ID No. 4, SEQ ID No. 6 or SEQ ID No. 8.

To achieve an amplification, for example the expression of the genes or alleles or the catalytic properties of the protein can be increased. If appropriate, both measures can be combined.

To achieve an overexpression, for example the number of copies of the corresponding genes can be increased, or the promoter and regulator region or the ribosome binding site which is located upstream of the structural gene can be mutated. Expression cassettes or promoters, which are incorporated upstream of the structural gene, act in a similar manner. By introducing inducible promoters, it is in addition possible to increase the expression in the course of production of L-threonine by fermentation. Measures to increase the lifetime of the m-RNA likewise improve the expression. In addition, by preventing the degradation of the enzyme protein, likewise the enzyme activity is increased. The genes or gene constructs can either be present in plasmids having varying numbers of copies, or be integrated into the chromosome and amplified. Alternatively, in addition, overexpression of the genes in question can be achieved by altering the media composition and culture conditions.

Methods for overexpression are sufficiently described in the prior art, for example in Makrides et al. (Microbiological Reviews 60 (3), 512-538 (1996)). By using vectors, the number of copies is increased by at least one (1) copy. As vectors, use can be made of plasmids such as, for example, as described in U.S. Pat. No. 5,538,873. As vectors, use can likewise be made of phages, for example the phage Mu, as described in EP 0 332 448, or the phage lambda (λ). An increase in the number of copies can also be achieved by a further copy being incorporated into a further position of the chromosome, for example, in the att site of phage λ (Yu and Court, Gene 223, 77-81 (1998)). U.S. Pat. No. 5,939,307 describes how an increase in expression could be achieved by incorporating expression cassettes or promoters such as, for example, tac promoter, trp promoter, lpp promoter or $P_L$ promoter and $P_R$ promoter of phage λ for example upstream of the chromosomal threonine operon. In a similar manner use can be made of promoters of phage T7, the gear-box promoters or the nar promoter. Such expression cassettes or promoters can also be used in order to overexpress plasmid-bound genes, as described in EP 0 593 792. The expression of plasmid-bound genes can in turn be controlled by using lacI$^Q$ allele (Glascock and Weickert, Gene 223, 221-231 (1998)).

Those skilled in the art will find instructions for this, inter alia, in Chang and Cohen (Journal of Bacteriology 134: 1141-1156 (1978)), in Hartley and Gregori (Gene 13: 347-353 (1981)), in Amann and Brosius (Gene 40: 183-190 (1985)), in de Broer et al. (Proceedings of the National Academy of Sciences of the United States of America 80: 21-25 (1983)), in LaVallie et al. (BIO/TECHNOLOGY 11: 187-193 (1993)), in PCT/US97/13359, in Llosa et al. (Plasmid 26: 222-224 (1991)), in Quandt and Klipp (Gene 80: 161-169 (1989)), in Hamilton et al. (Journal of Bacteriology 171: 4617-4622 (1989)), in Jensen and Hammer (Biotechnology and Bioengineering 58: 191-195 (1998)) and in known textbooks of genetics and molecular biology.

Use can be made of plasmid vectors which can be replicated in Enterobacteriaceae, such as, for example, cloning vectors derived from pACYC184 (Bartolomé et al.; Gene 102: 75-78 (1991)), pTrc99A (Amann et al.; Gene 69: 301-315 (1988)) or pSC101 derivatives (Vocke and Bastia; Proceedings of the National Academy of Sciences USA 80(21): 6557-6561 (1983)). In a method according to the invention, use can be made of a strain transformed by a plasmid vector, the plasmid vector carrying at least one lamB gene or allele or nucleotide sequences coding for its gene product LamB.

The term transformation is taken to mean the incorporation of an isolated nucleic acid by a host (microorganism).

It is likewise possible to transfer mutations which relate to the expression of the respective genes to various strains by sequence exchange (Hamilton et al.; Journal of Bacteriology 171: 4617-4622 (1989)), conjugation or transduction.

More detailed explanations of the terms of genetics and molecular biology can be found in known textbooks of genetics and molecular biology such as, for example, the textbook by Birge (Bacterial and Bacteriophage Genetics, 4th edition, Springer Verlag, New York (USA), 2000) or the textbook by Berg, Tymoczko and Stryer (Biochemistry, 5th edition, Freeman and Company, New York (USA), 2002) or the handbook by Sambrook et al. (Molecular Cloning, A Laboratory Manual (3-volume set), Cold Spring Harbor Laboratory Press, Cold Spring Harbor (USA), 2001).

In addition, it can be advantageous for the production of L-amino acids, in particular L-threonine, using strains of the family Enterobacteriaceae, in addition to the amplification of the lamB gene, to amplify one or more enzymes of the known threonine biosynthesis pathway or enzymes of anaplerotic metabolism or enzymes for the production of reduced nicotinamide adenine dinucleotide phosphate or enzymes of glycolysis or PTS enzymes or enzymes of sulfur metabolism. The use of endogenous genes is generally preferred.

For instance, it is possible, for example, to amplify, in particular overexpress, simultaneously one or more of the genes selected from the group at least one gene of the thrABC operon coding for aspartate kinase, homoserine dehydrogenase, homoserine kinase and threonine synthase (U.S. Pat. No. 4,278,765), the pyc gene of *Corynebacterium glutamicum* coding for pyruvate carboxylase (WO 99/18228), the pps gene coding for phosphoenolpyruvate synthase (Molecular and General Genetics 231(2): 332-336 (1992)), the ppc gene coding for phosphoenolpyruvate carboxylase (WO 02/064808), the genes pntA and pntB coding for the subunits of pyridine transhydrogenase (European Journal of Biochemistry 158: 647-653 (1986)), the gene rhtB coding for the protein conferring homoserine resistance (EP-A-0 994 190), the gene rhtC coding for the protein conferring threonine resistance (EP-A-1 013 765), the thrE gene from *Corynebacterium glutamicum* coding for the threonine-export-carrier protein (WO 01/92545), the gdhA gene coding for glutamate dehydrogenase (Nucleic Acids Research 11; 5257-5266 (1983); gene 23: 199-209 (1983)), the pgm gene coding for phosphoglucomutase (WO 03/004598), the fba gene coding for fructose biphosphate aldolase (WO 03/004664), the ptsH gene of the ptsHIcrr operon coding for the phosphohistidine protein hexose phosphotransferase of the phosphotransferase system PTS (WO 03/004674), the ptsI gene of the ptsHIcrr operon coding for enzyme I of the phosphotransferase system PTS (WO 03/004674), the crr gene of the ptsHIcrr operon coding for the glucose-specific IIA component of the phosphotransferase system PTS (WO 03/004674), the ptsG gene coding for the glucose-specific IIBC component (WO 03/004670), the lrp gene coding for the regulator of the leucine regulon (WO 03/004665), the fadR gene coding for the regulator of the fad regulon (WO 03/038106), the iclR gene coding for the regulator of central intermediate metabolism (WO 03/038106), the ahpC gene of the ahpCF operon coding for the small subunit of alkyl hydroperoxide reductase (WO 03/004663), the ahpF gene of the ahpCF operon coding for the large subunit of alkyl hydroperoxide reductase (WO 03/004663), the cysK gene coding for cysteine synthase A (WO 03/006666), the cysB gene coding for the regulator of the cys regulon (WO 03/006666), the cysJ gene of the cysJIH operon coding for the flavoprotein of the NADPH sulfite reductase (WO 03/006666), the cysI gene of the cysJIH operon coding for the hemoprotein of NADPH sulfite reductase (WO 03/006666), the cysH gene of the cysJIH operon coding for adenylyl-sulfate reductase (WO 03/006666), the rseA gene of the rseABC operon coding for a membrane protein having anti-sigmaE activity (WO 03/008612), the rseC gene of the rseABC operon coding for a global regulator of the sigmaE factor (WO 03/008612), the sucA gene of the sucABCD operon coding for the decarboxylase subunit of 2-ketoglutarate dehydrogenase (WO 03/008614), the sucB gene of the sucABCD operon coding for the dihydrolipoyltranssuccinase E2 subunit of 2-ketoglutarate dehydrogenase (WO 03/008614), the sucC gene of the sucABCD operon coding for the β-subunit of succinyl-CoA synthetase (WO 03/008615)

the sucD gene of the sucABCD operon coding for the α-subunit of succinyl-CoA synthetase (WO 03/008615), the aceE gene coding for the E1 component of the pyruvate dehydrogenase complex (WO 03/076635), the aceF gene coding for the E2 component of the pyruvate dehydrogenase complex (WO 03/076635), the rseB gene coding for the regulator of the sigmaE factor activity (Molecular Microbiology 24(2): 355-371 (1997)), the malT gene coding for the positive transcriptional regulator of the maltose regulon (Gene 42: 201-208 (1986), DE102004003411.7), the gene product of the open reading frame (ORF) yaaU of *Escherichia coli* (Accession Number AE000114 of the National Center for Biotechnology Information (NCBI, Bethesda, Md., USA), DE10361268.8), the gene product of the open reading frame (ORF) yodA of *Escherichia coli* (Accession Number AE000288 of the National Center for Biotechnology Information (NCBI, Bethesda, Md., USA), DE10361192.4), the gene product of the open reading frame (ORF) yibD of *Escherichia coli* (Accession Number AE000439 of the National Center for Biotechnology Information (NCBI, Bethesda, Md., USA), DE102004005836.9).

In addition, for the production of L-amino acids, in particular L-threonine, it can be advantageous, in addition to amplification of the lamB gene, to attenuate, in particular switch off, or reduce the expression of one or more of the genes selected from the group the tdh gene coding for threonine dehydrogenase (Journal of Bacteriology 169: 4716-4721 (1987)), the mdh gene coding for malate dehydrogenase (E.C. 1.1.1.37) (Archives in Microbiology 149: 36-42 (1987)), the gene product of the open reading frame (ORF) yjfA of *Escherichia coli* (Accession Number AAC77180 of the National Center for Biotechnology Information (NCBI, Bethesda, Md., USA), WO 02/29080), the gene product of the open reading frame (ORF) ytfP of *Escherichia coli* (Accession Number AAC77179 of the National Center for Biotechnology Information (NCBI, Bethesda, Md., USA), WO 02/29080), the pckA gene coding for the enzyme phosphoenolpyruvate carboxykinase (WO 02/29080), the poxB gene coding for pyruvate oxidase (WO 02/36797), the dgsA gene coding for the DgsA regulator of the phosphotransferase system (WO 02/081721), which gene is also known under the name mlc gene, the fruR gene coding for the fructose repressor (WO 02/081698), which gene is also known under the name cra gene, the rpoS gene coding for the Sigma$^{38}$ factor (WO 01/05939), which gene is also known under the name katF gene and the aspA gene coding for aspartate ammonium lyase (WO 03/008603).

The expression "attenuation" in this context describes reducing or switching off the intracellular activity or concentration of one or more enzymes or proteins in a microorganism which are coded for by the corresponding DNA by using, for example, a weaker promoter than in the original strain or a gene or allele which codes for a corresponding enzyme or protein having a lower activity, or inactivating the corresponding enzyme or protein or the gene and, if appropriate, combining these measures.

By means of the attenuation measures, the activity or concentration of the corresponding protein is generally lowered to 0 to 75%, 0 to 50%, 0 to 25%, 0 to 10%, or 0 to 5%, of the activity or concentration of the wild type protein, or of the activity or concentration of the protein in the non-recombinant starting microorganism. The starting microorganism or parent strain is taken to mean the microorganism on which the inventive measures are carried out.

To achieve attenuation, for example the expression of the genes or open reading frames or the catalytic properties of the enzyme proteins can be reduced or switched off. If appropriate, both measures can be combined.

Reduction of gene expression can be performed by suitable culture conditions, by genetic modification (mutation) of the signal structures of gene expression or else by antisense-RNA technique. Signal structures of gene expression are, for example, repressor genes, activator genes, operators, promoters, attenuators, ribosome binding sites, the start codon and terminators. Those skilled in the art will find information on this, inter alia, for example in Jensen and Hammer (Biotechnology and Bioengineering 58: 191-195 (1998)), in Carrier and Keasling (Biotechnology Progress 15: 58-64 (1999)), Franch and Gerdes (Current Opinion in Microbiology 3: 159-164 (2000)) and in known textbooks of genetics and molecular biology such as, for example, the textbook by Knippers ("Molekulare Genetik" [Molecular Genetics], 6th edition, Georg Thieme Verlag, Stuttgart, Germany, 1995) or that by Winnacker ("Gene und Klone" [Genes and Clones], VCH Verlagsgesellschaft, Weinheim, Germany, 1990).

Mutations which lead to a modification or reduction of the catalytic properties of enzyme proteins are known from the prior art. Examples which may be mentioned are the works by Qiu and Goodman (Journal of Biological Chemistry 272: 8611-8617 (1997)), Yano et al. (Proceedings of the National Academy of Sciences of the United States of America 95: 5511-5515 (1998)), Wente and Schachmann (Journal of Biological Chemistry 266: 20833-20839 (1991)).

Summarizing explanations can be taken from known textbooks of genetics and molecular biology such as, for example, that by Hagemann ("Allgemeine Genetik" [General Genetics], Gustav Fischer Verlag, Stuttgart, 1986).

As mutations, transitions, transversions, insertions and deletions of at least one (1) base pair or nucleotide come into consideration. Depending on the action of the amino acid replacement caused by the mutation on the enzyme activity, these are described as missense mutations or nonsense mutations. A missense mutation leads to a replacement of a given amino acid in a protein for another, this being in particular a non-conservative amino acid replacement. As a result the functionality or activity of the protein is impaired and reduced to a value of 0 to 75%, 0 to 50%, 0 to 25%, 0 to 10%, or 0 to 5%. A nonsense mutation leads to a stop codon in the coding region of the gene and thus to premature termination of translation. Insertions or deletions of at least one base pair in a gene lead to frame shift mutations which lead to wrong amino acids being incorporated or to translation being prematurely terminated. If as a consequence of the mutation a stop codon is produced in the coding region, this likewise leads to premature termination of translation. Deletions of at least one (1) codon or a plurality of codons typically likewise lead to complete loss of enzyme activity.

Instructions on producing such mutations are part of the prior art and can be taken from known textbooks of genetics and molecular biology such as, for example, the textbook by Knippers ("Molekulare Genetik" [Molecular Genetics], 6th edition, Georg Thieme Verlag, Stuttgart, Germany, 1995), that by Winnacker ("Gene und Klone" [Genes and Clones], VCH Verlagsgesellschaft, Weinheim, Germany, 1990) or that by Hagemann ("Allgemeine Genetik" [General Genetics], Gustav Fischer Verlag, Stuttgart, 1986).

Suitable mutations in the genes can be incorporated into suitable strains by gene or allele replacement.

A conventional method is the method described by Hamilton et al. (Journal of Bacteriology 171: 4617-4622 (1989)) of gene replacement using a conditionally replicating pSC101 derivative pMAK705. It is likewise possible to make use of other methods described in the prior art such as, for example, that of Martinez-Morales et al. (Journal of Bacteriology 181: 7143-7148 (1999)) or that of Boyd et al. (Journal of Bacteriology 182: 842-847 (2000)).

It is likewise possible to transfer mutations in the respective genes or mutations which relate to the expression of the respective genes or open reading frames to various strains by conjugation or transduction.

In addition, it can be advantageous for the production of L-amino acids, in particular L-threonine, in addition to amplification of the lamB gene, to switch off unwanted side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention can be cultured in the batch method, the fed batch method, the repeated fed batch method or a continuous method. Known culture methods are summarized in the textbook by Chmiel (Bioprozesstechnik 1. Einführung in die Bioverfahrenstechnik [Bioprocess Engineering 1. Introduction to Bioprocess Engineering] (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must satisfy in a suitable manner the requirements of the respective strains. Descriptions of culture media of various microorganisms are given in the handbook "Manual of Methods for General Bacteriology" of the American Society for Bacteriology (Washington D.C., USA, 1981).

As carbon source, use can be made of sugars and carbohydrates such as, for example, glucose, sucrose, lactose, fructose, maltose, molasses, starch and if appropriate cellulose, oils and fats such as, for example, soybean oil, sunflower oil, peanut oil and coconut fat, fatty acids such as, for example, palmitic acid, stearic acid and linoleic acid, alcohols such as, for example, glycerol and ethanol, and organic acids such as, for example, acetic acid. These substances can be used individually or as a mixture.

As nitrogen source, use can be made of organic nitrogenous compounds such as peptones, yeast extract, meat extract, malt extract, corn steep water, soybean flour and urea or inorganic compounds such as ammonium sulfate, ammonium chloride, ammonium phosphate, ammonium carbonate and ammonium nitrate. The nitrogen sources can be used individually or as a mixture.

As phosphorus source, use can be made of phosphoric acid, potassium dihydrogen phosphate or dipotassium hydrogen phosphate or the corresponding sodium-containing salts. The culture medium must, in addition, contain salts of metals such as, for example, magnesium sulfate or iron sulfate, which are necessary for growth. Finally, essential growth substances such as amino acids and vitamins can be used in addition to the abovementioned substances. Furthermore, suitable precursors can be added to the culture medium. Said starting materials can be added to the culture in the form of a single batch or in a suitable manner fed during culturing.

The fermentation is carried out generally at a pH of 5.5 to 9.0, in particular 6.0 to 8.0. For pH control of the culture, use is made of basic compounds such as sodium hydroxide, potassium hydroxide, ammonia or ammonia water, or acidic compounds such as phosphoric acid or sulfuric acid in a suitable manner. For control of foam development, antifoams such as, for example, polyglycol esters of fatty acids can be used. To maintain the stability of plasmids, suitable selective substances such as antibiotics can be added to the medium. In order to maintain aerobic conditions, oxygen or oxygen-containing gas mixtures such as, for example, air are introduced into the culture. The temperature of the culture is usually 25° C. to 45° C., and preferably 30° C. to 40° C. The culture is continued until a maximum of L-amino acids or L-threonine has formed. This target is usually reached within 10 hours to 160 hours.

L-Amino acids can be analyzed by anion-exchange chromatography with subsequent ninhydrin derivatization, as described in Spackman et al. (Analytical Chemistry 30: 1190-1206 (1958)), or by reversed phase HPLC, as described by Lindroth et al. (Analytical Chemistry 51: 1167-1174 (1979)).

The inventive method serves for production by fermentation of L-amino acids, such as, for example, L-threonine, L-isoleucine, L-valine, L-methionine, L-homoserine, L-tryptophan and L-lysine, in particular L-threonine.

The present invention will be described in more detail hereinafter with reference to examples.

Minimal media (M9) and complete media (LB) used for *Escherichia coli* are described by J. H. Miller (A Short Course in Bacterial Genetics (1992), Cold Spring Harbor Laboratory Press). Isolation of plasmid DNA from *Escherichia coli* and all techniques of restriction, ligation, Klenow and alkaline phosphatase treatment are carried out as in Sambrook et al. (Molecular Cloning—A Laboratory Manual (1989) Cold Spring Harbor Laboratory Press). The transformation of *Escherichia coli*, unless described otherwise, is carried out according to Chung et al. (Proceedings of the National Academy of Sciences of the United States of America 86: 2172-2175 (1989)).

The incubation temperature in the production of strains and transformants is 37° C.

EXAMPLE 1

Construction of the Expression Plasmid pTrc99AlamB

The lamB gene from *E. coli* K12 is amplified using the polymerase chain reaction (PCR) and also synthetic oligonucleotides. Starting from the nucleotide sequence of the lamB gene in *E. coli* K12 MG1655 (Accession Number AE000477), Blattner et al. (Science 277: 1453-1474 (1997)), PCR primers are synthesized (MWG Biotech, Ebersberg, Germany). The sequences of the primers are modified in such a manner that recognition sites for restriction enzymes are produced. For the P_lam1neu primer the recognition sequence for XbaI is used, and for the P_lam2neu primer, the recognition sequence for HindIII is chosen, which sequences are marked in the nucleotide sequence illustrated below by underscores:

P_lam1neu:
5'-TCTAGAGCCTGTCACAGGTGATGTGAA-3'  (SEQ ID No. 1)

P_lam2neu:
5'-AAGCTTACAGCCGTTGTAGGCCTGATA-3'  (SEQ ID No. 2)

The chromosomal *E. coli* K12 MG1655 DNA used for the PCR is isolated, according to the manufacturer's details, with "Qiagen Genomic-tips 100/G" (QIAGEN, Hilden, Germany). A 1498 bp DNA fragment can be amplified using the specific primers under standard PCR conditions (Innis et al. (1990) PCR Protocols. A Guide to Methods and Applications, Academic Press) with the Vent-DNA-Polymerase (New England Biolaps GmbH, Frankfurt, Germany) (SEQ ID No. 3).

The amplified lamB fragment is, in accordance with the manufacturer's details, ligated with the vector pCR-Blunt II-TOPO (Zero TOPO TA Cloning Kit, Invitrogen, Groningen, Netherlands) and transformed into the *E. coli* strain TOP10. Plasmid-carrying cells are selected on LB agar which is admixed with 50 µg/ml of kanamycin. After the isolation of plasmid DNA, the vector is cleaved using the enzymes EcoRI and EcoRV and after examination of the cleavage in 0.8% strength agarose gel is termed pCRB1untlamB.

The nucleotide sequence of the amplified DNA fragment or PCR product is examined by the dideoxy chain break method of Sanger et al. (Proceedings of the National Academy of Sciences U.S.A., 74: 5463-5467 (1977)) using the "ABI Prism 377" sequencing instrument from PE Applied Biosystems (Weiterstadt, Germany). The sequence of the PCR product corresponds to positions 1-1498 of the sequence shown in SEQ ID No. 3. The amino acid sequence of the associated LamB protein is shown in SEQ ID No. 4.

Subsequently, the vector pCRBluntlamB is cleaved using the enzymes HindIII and XbaI and the approximately 1500 bp lamB fragment, after resolution in an 0.8% strength agarose gel is isolated from the gel (QIAquick Gel Extraction Kit, QIAGEN, Hilden, Germany) and ligated to the vector pTrc99A (Pharmacia Biotech, Uppsala, Sweden), which has been digested by the enzymes HindIII and XbaI. The *E. coli* strain DH5a (Grant et al.; Proceedings of the National Academy of Sciences USA, 87 (1990) 4645-4649) is transformed by the ligation approach and plasmid-carrying cells are selected on LB agar which is admixed with 50 µg/ml of ampicillin.

Successful cloning can be demonstrated after plasmid DNA isolation by control cleavage using the enzymes EcoRV and SspI.

The plasmid is called pTrc99AlamB (FIG. 1).

EXAMPLE 2

Construction of the Expression Plasmid pMW218lamB

The vector pCRBluntlamB described in example 1 is cleaved using the enzymes HindIII and XbaI and the lamB fragment, after resolution in a 0.8% strength agarose gel, is isolated from the gel (QIAquick Gel Extraction Kit, QIAGEN, Hilden, Germany) and ligated to the low-copy vector pMW218 (Nippon Gene, Toyama, Japan), which has been digested using the enzymes HindIII and XbaI. The *E. coli* strain DH5α (Grant et al.: Proceedings of the National Academy of Sciences USA, 87 (1990) 4645-4649) is transformed by the ligation approach and plasmid-carrying cells are selected on LB agar which is admixed with 50 µg/ml of kanamycin.

Successful cloning can be demonstrated after plasmid DNA isolation by control cleavage using the enzyme ClaI.

The plasmid is called pMW218lamB (FIG. 2).

EXAMPLE 3

Production of L-Threonine Using the Strains MG442/pTrc99AlamB and MG442/pMW218lamB The L-threonine-producing *E. coli* strain MG442 is described in U.S. Pat. No. 4,278,765 and is deposited as CMIM B-1628 in the Russian National Collection for Industrial Microorganisms (VKPM, Moscow, Russia).

Strain MG442 is transformed using the expression plasmids pTrc99AlamB and pMW218lamB described in example 1 and 2 and the vectors pTrc99A and pMW218 and plasmid-carrying cells are selected on LB agar containing 50 µg/ml of ampicillin or 50 µg/ml of kanamycin. In this manner the strains MG442/pTrc99AlamB, MG442/pTrc99A, MG442/pMW218lamB and MG442/pMW218 are formed. Selected individual colonies are subsequently further grown on minimal medium with the following composition: 3.5 g/l of $Na_2HPO_4.2H_2O$, 1.5 g/l of $KH_2PO_4$, 1 g/l of $NH_4Cl$, 0.1 g/l of $MgSO_4.7H_2O$, 2 g/l of glucose, 20 g/l of agar, 50 mg/l of ampicillin or 50 mg/l of kanamycin. The formation of L-threonine is studied in batch cultures of 10 ml which are contained in 100 ml conical flasks. To this is added 10 ml of preculture medium of the following composition: 2 g/l of yeast extract, 10 g/l of $(NH_4)_2SO_4$, 1 g/l of $KH_2PO_4$, 0.5 g/l of $MgSO_4.7H_2O$, 15 g/l of $CaCO_3$, 20 g/l of glucose, 50 mg/l of ampicillin or 50 mg/l of kanamycin, inoculated and incubated for 16 hours at 37° C. and 180 rpm on an ESR incubator from Kühner AG (Birsfelden, Switzerland). 250 µl samples of this preculture are each inoculated into 10 ml of production medium (25 g/l of $(NH_4)_2SO_4$, 2 g/l of $KH_2PO_4$, 1 g/l of $MgSO_4.7H_2O$, 0.03 g/l of $FeSO_4.7H_2O$, 0.018 g/l of $MnSO_4.1H_2O$, 30 g/l of $CaCO_3$, 20 g/l of glucose, 50 mg/l of ampicillin or 50 mg/l of kanamycin) and incubated for 48 hours at 37° C. After incubation, the optical density (OD) of the culture suspension is determined using an LP2W photometer from Dr Lange (Düsseldorf, Germany) at a measurement wavelength of 660 nm.

Subsequently, the concentration of L-threonine formed is determined in the sterile-filtered culture supernatant using an amino acid analyzer from Eppendorf-BioTronik (Hamburg, Germany) by ion-exchange chromatography and post-column reaction using ninhydrin detection.

Table 1 shows the result of the experiment.

TABLE 1

| Strain | OD (660 nm) | L-Threonine g/l |
|---|---|---|
| MG442/pTrc99A | 2.0 | 2.1 |
| MG442/pTrc99AlamB | 2.0 | 2.6 |
| MG442/pMW218 | 6.2 | 1.7 |
| MG442/pMW218lamB | 5.7 | 2.5 |

BRIEF DESCRIPTION OF THE FIGURES

FIG. 1: map of the plasmid pTrc99AlamB containing the lamB gene

FIG. 2: map of the plasmid pMW218lamB containing the lamB gene

Length details are to be considered as approximate data. The abbreviations and names used have the following meanings:

bla: gene which codes for ampicillin resistance kan: gene which codes for kanamycin resistance lac Iq: gene for the repressor protein of the trc promoter lacZ': gene fragment which codes for the α-peptide of β-galactosidase trc: trc promoter region, IPTG inducible
lamB: coding region of the lamB gene
5S: 5S rRNA region
rrnBT: rRNA terminator region The abbreviations for the restriction enzymes have the following meanings:

XbaI: restriction endonuclease from *Xanthomonas badrii*
HindIII: restriction endonuclease from *Haemophilus influenzae*
ClaI: restriction endonuclease from *Caryophanon latum*
SspI: restriction endonuclease from *Sphaerotilus* species
EcoRV: restriction endonuclease from *Escherichia coli*

The invention claimed is:

1. A recombinant microorganism of the family Enterobacteriaceae which, relative to the corresponding nonrecombinant microorganism:
   a) comprises a lamB gene which is amplified or overexpressed by increasing the copy number of the lamB gene or by putting the lamB gene under the control of a strong promoter; and wherein said lamB gene codes for a polypeptide which:
      i) has at least 90% sequence identity to the amino acid sequence of SEQ ID NO:4; and
      ii) has maltoporin activity;
   (b) further comprises at least one gene in a biosynthesis pathway of an L-amino acid that is amplified or overexpressed: and
   (c) produces an increased amount of L-amino acids.

2. The recombinant microorganism of claim 1, wherein said polypeptide comprises an amino acid sequence at least 9500 identical to the sequence of SEQ ID NO:4.

3. The recombinant microorganism of claim 1, wherein said polypeptide comprises an amino acid sequence identical to that of SEQ ID NO:4.

4. The recombinant microorganism of claim 1, produced by transformation, transduction, conjugation or a combination of these methods using a vector which comprises the lamB gene, or an allele of this gene and a promoter that is operably linked to said gene or said allele.

5. The recombinant microorganism of claim 1, wherein the number of copies of said lamB gene is increased by at least 1.

6. The recombinant microorganism of claim 5, wherein the number of copies of the lamB gene is increased by integration of the lamB gene into the chromosome of a microorganism.

7. The recombinant microorganism of claim 5, wherein the number of copies of the lamB gene is increased by a vector replicating extrachromosomally.

8. The recombinant microorganism of claim 1, wherein said lamB gene is under the control of a promoter amplifying the expression of the gene.

9. The recombinant microorganism of claim 1, wherein the concentration or activity of the lamB gene product is increased by at least 10%, relative to the corresponding nonrecombinant starting strain.

10. The recombinant microorganism of claim 1, wherein said recombinant microorganism is selected from the group of genera consisting of: Escherichia, Erwinia, Providencia and Serratia.

11. The recombinant microorganism of claim 1, wherein one of said amino acids is L-threonine.

12. The recombinant microorganism of claim 11, produced by transformation, transduction, conjugation or a combination of these methods using a vector which comprises the lamB gene or an allele of this gene and a promoter that is operably linked to said gene or said allele.

13. A method for producing a desired L-amino acid by fermentation, comprising:
   a) culturing a recombinant microorganism of the family Enterobacteriaceae that produces the desired L-amino acid and wherein:
      i) relative to the corresponding nonrecombinant microorganism, said recombinant microorganism overexpresses a lamB gene or a polynucleotide coding for a polypeptide which is at least 9000 sequence identical to the polypeptide of SEQ ID NO:4 and wherein said polypeptide has maltoporin activity;
      ii) said culturing is performed in a medium and under conditions in which the desired L-amino acid is enriched in the medium or in the cells, and
   b) isolating the desired L-amino acid along with 0 to 100% of the components of the fermentation broth and/or the biomass.

14. The method of claim 13, wherein said desired L-amino acid is L-threonine, and wherein, in addition to lamB, said recombinant microorganism comprises at least one additional gene that is amplified or overexpressed, said additional gene being selected from the group consisting of:
   a) at least one gene of the thrABC operon coding for aspartate kinase, homoserine dehydrogenase, homoserine kinase and threonine synthase,
   b) the pyc gene of Corynebacterium glutamicum coding for pyruvate carboxylase,
   c) the pps gene coding for phosphoenolpyruvate synthase,
   d) the ppc gene coding for phosphoenolpyruvate carboxylase,
   e) the genes pntA and pntB coding for the subunits of pyridine transhydrogenase,
   f) the gene rhtB coding for the protein conferring homoserine resistance,
   g) the gene rhtC coding for the protein conferring threonine resistance,
   h) the thrE gene from Corynebacterium glutamicum coding for the threonine-export-carrier protein,
   i) the gdhA gene coding for glutamate dehydrogenase,
   j) the pgm gene coding for phosphoglucomutase,
   k) the fba gene coding for fructose biphosphate aldolase,
   l) the ptsH gene coding for phosphohistidine protein hexose phosphotransferase,
   m) the ptsI gene coding for enzyme I of the phosphotransferase system,
   n) the crr gene coding for the glucose-specific IIA component,
   o) the ptsG gene coding for the glucose-specific IIBC component, p) the lrp gene coding for the regulator of the leucine regulon,
q) the fadR gene coding for the regulator of the fad regulon,
r) the iclR gene coding for the regulator of central intermediate metabolism,
s) the ahpC gene coding for the small subunit of alkyl hydroperoxide reductase,
t) the ahpF gene coding for the large subunit of alkyl hydroperoxide reductase,
u) the cysK gene coding for cysteine synthase A,
v) the cysB gene coding for the regulator of the cys regulon,
w) the cysJ gene coding for the flavoprotein of NADPH sulfite reductase,
x) the cysI gene coding for the hemoprotein of NADPH sulfite reductase,
y) the cysH gene coding for adenylylsulfate reductase,
z) the rseA gene coding for a membrane protein having anti-sigmaE activity,
aa) the rseC gene coding for a global regulator of the sigmaE factor,
bb) the sucA gene coding for the decarboxylase subunit of 2-ketoglutarate dehydrogenase,
cc) the sucB gene coding for the dihydrolipoyltranssuccinase E2 subunit of 2-ketoglutarate dehydrogenase,
dd) the sucC gene coding for the β-subunit of succinyl-CoA synthetase,
ee) the sucD gene coding for the α-subunit of succinyl-CoA synthetase,
ff) the E gene coding for the E1 component of the pyruvate dehydrogenase complex,
gg) the aceF gene coding for the E2 component of the pyruvate dehydrogenase complex,
hh) the rseB gene coding for the regulator of SigmaE factor activity,
ii) the malT gene coding for the positive transcriptional regulator of the maltose regulon,
jj) the gene product of the open reading frame (ORF) yaaU of *Escherichia coli,*
kk) the gene product of the open reading frame (ORF) yodA of *Escherichia coli* and
ll) the gene product of the open reading frame (ORF) yibD of *Escherichia coli.*

15. The method of claim 13, wherein said recombinant microorganism further comprises at least one metabolic pathway which reduces the formation of the desired L-amino acid that is at least in part attenuated.

16. The method of claim 15, wherein said desired L-amino acid is L-threonine, and wherein said recombinant microorganism comprises at least one gene that is disrupted, said additional one gene being selected from the group consisting of:
a) the tdh gene coding for threonine dehydrogenase,
b) the mdh gene coding for malate dehydrogenase,
c) the gene product of the open reading frame (ORF) yjfA of *Escherichia coli,*
d) the gene product of the open reading frame (ORF) ytfP of *Escherichia coli,*
e) the pckA gene coding for phosphoenolpyruvate carboxykinase,
f) the poxB gene coding for pyruvate oxidase,
g) the dgsA gene coding for the DgsA regulator of the phosphotransferase system,
h) the fruR gene coding for the fructose repressor,
i) the rpoS gene coding for the Sigma$^{38}$ factor, and
j) the aspA gene coding for aspartate ammonium lyase.

17. The method of claim 13, wherein said desired L-amino acid is selected from the group consisting of: L-asparagine, L-serine, L-glutamate, L-glycine, L-alanine, L-cysteine, L-valine, L-methionine, L-proline, L-isoleucine, L-leucine, L-tyrosine, L-phenylalanine, L-histidine, L-lysine, L-tryptophan, L-arginine and L-homoserine.

18. The method of claim 13, wherein said desired L-amino acid is L-threonine.

19. The method of claim 18, wherein said recombinant microorganism is produced by transformation, transduction, conjugation or a combination of these methods using a vector which comprises the lamB gene or an allele of this gene and a promoter that is operably linked to said gene or said allele.

* * * * *

```
                              SEQUENCE LISTING

<160> NUMBER OF SEQ ID NOS: 8

<210> SEQ ID NO 1
<211> LENGTH: 27
<212> TYPE: DNA
<213> ORGANISM: Artificial
<220> FEATURE:
<221> NAME/KEY: Primer
<222> LOCATION: (1)..(27)
<223> OTHER INFORMATION: chemically synthesized
<220> FEATURE:
<221> NAME/KEY: Restriction site
<222> LOCATION: (1)..(6)
<223> OTHER INFORMATION: chemically synthesized

<400> SEQUENCE: 1
tctagagcct gtcacaggtg atgtgaa                                      27

<210> SEQ ID NO 2
<211> LENGTH: 27
<212> TYPE: DNA
<213> ORGANISM: Artificial
<220> FEATURE:
<221> NAME/KEY: Primer
<222> LOCATION: (1)..(27)
<223> OTHER INFORMATION: chemically synthesized
<220> FEATURE:
<221> NAME/KEY: Restriction site
<222> LOCATION: (1)..(6)
<223> OTHER INFORMATION: chemically synthesized

<400> SEQUENCE: 2
aagcttacag ccgttgtagg cctgata                                      27

<210> SEQ ID NO 3
<211> LENGTH: 1498
<212> TYPE: DNA
<213> ORGANISM: Escherichia coli
<220> FEATURE:
<221> NAME/KEY: PCR product
<222> LOCATION: (1)..(1498)
<223> OTHER INFORMATION: lamB PCR product
<220> FEATURE:
<221> NAME/KEY: primer_bind
<222> LOCATION: (1)..(27)
<223> OTHER INFORMATION: Primer P_lam1neu
<220> FEATURE:
<221> NAME/KEY: CDS
<222> LOCATION: (57)..(1397)
<223> OTHER INFORMATION: lamB coding region
<220> FEATURE:
<221> NAME/KEY: primer_bind
<222> LOCATION: (1472)..(1498)
<223> OTHER INFORMATION: Primer P_lam2neu

<400> SEQUENCE: 3
tctagagcct gtcacaggtg atgtgaaaaa agaaaagcaa tgactcagga gataga atg      59
                                                             Met
                                                              1 atg att act ctg cgc aaa ctt cct ctg gcg gtt gcc gtc gca gcg ggc      107
Met Ile Thr Leu Arg Lys Leu Pro Leu Ala Val Ala Val Ala Ala Gly
```

```
                  5                      10                     15
gta atg tct gct cag gca atg gct gtt gat ttc cac ggc tat gca cgt      155
Val Met Ser Ala Gln Ala Met Ala Val Asp Phe His Gly Tyr Ala Arg
         20                  25                  30 tcc ggt att ggt tgg aca ggt agc ggt ggt gaa caa cag tgt ttc cag      203
Ser Gly Ile Gly Trp Thr Gly Ser Gly Gly Glu Gln Gln Cys Phe Gln
 35                  40                  45 act acc ggt gct caa agt aaa tac cgt ctt ggc aac gaa tgt gaa act      251
Thr Thr Gly Ala Gln Ser Lys Tyr Arg Leu Gly Asn Glu Cys Glu Thr
 50                  55                  60                  65 tat gct gaa tta aaa ttg ggt cag gaa gtg tgg aaa gag ggc gat aag      299
Tyr Ala Glu Leu Lys Leu Gly Gln Glu Val Trp Lys Glu Gly Asp Lys
                     70                  75                  80 agc ttc tat ttc gac act aac gtg gcc tat tcc gtc gca caa cag aat      347
Ser Phe Tyr Phe Asp Thr Asn Val Ala Tyr Ser Val Ala Gln Gln Asn
                 85                  90                  95 gac tgg gaa gct acc gat ccg gcc ttc cgt gaa gca aac gtg cag ggt      395
Asp Trp Glu Ala Thr Asp Pro Ala Phe Arg Glu Ala Asn Val Gln Gly
             100                 105                 110 aaa aac ctg atc gaa tgg ctg cca ggc tcc acc atc tgg gca ggt aag      443
Lys Asn Leu Ile Glu Trp Leu Pro Gly Ser Thr Ile Trp Ala Gly Lys
         115                 120                 125 cgc ttc tac caa cgt cat gac gtt cat atg atc gac ttc tac tac tgg      491
Arg Phe Tyr Gln Arg His Asp Val His Met Ile Asp Phe Tyr Tyr Trp
130                 135                 140                 145 gat att tct ggt cct ggt gcc ggt ctg gaa aac atc gat gtt ggc ttc      539
Asp Ile Ser Gly Pro Gly Ala Gly Leu Glu Asn Ile Asp Val Gly Phe
                 150                 155                 160 ggt aaa ctc tct ctg gca gca acc cgc tcc tct gaa gct ggt ggt tct      587
Gly Lys Leu Ser Leu Ala Ala Thr Arg Ser Ser Glu Ala Gly Gly Ser
             165                 170                 175 tcc tct ttc gcc agc aac aat att tat gac tat acc aac gaa acc gcg      635
Ser Ser Phe Ala Ser Asn Asn Ile Tyr Asp Tyr Thr Asn Glu Thr Ala
         180                 185                 190 aac gac gtt ttc gat gtg cgt tta gcg cag atg gaa atc aac ccg ggc      683
Asn Asp Val Phe Asp Val Arg Leu Ala Gln Met Glu Ile Asn Pro Gly
     195                 200                 205 ggc aca tta gaa ctg ggt gtc gac tac ggt cgt gcc aac ttg cgt gat      731
Gly Thr Leu Glu Leu Gly Val Asp Tyr Gly Arg Ala Asn Leu Arg Asp
210                 215                 220                 225 aac tat cgt ctg gtt gat ggc gca tcg aaa gac ggc tgg tta ttc act      779
Asn Tyr Arg Leu Val Asp Gly Ala Ser Lys Asp Gly Trp Leu Phe Thr
                 230                 235                 240 gct gaa cat act cag agt gtc ctg aag ggc ttt aac aag ttt gtt gtt      827
Ala Glu His Thr Gln Ser Val Leu Lys Gly Phe Asn Lys Phe Val Val
             245                 250                 255 cag tac gct act gac tcg atg acc tcg cag ggt aaa ggg ctg tcg cag      875
Gln Tyr Ala Thr Asp Ser Met Thr Ser Gln Gly Lys Gly Leu Ser Gln
         260                 265                 270 ggt tct ggc gtt gca ttt gat aac gaa aaa ttt gcc tac aat atc aac      923
Gly Ser Gly Val Ala Phe Asp Asn Glu Lys Phe Ala Tyr Asn Ile Asn
     275                 280                 285 aac aac ggt cac atg ctg cgt atc ctc gac cac ggt gcg atc tcc atg      971
Asn Asn Gly His Met Leu Arg Ile Leu Asp His Gly Ala Ile Ser Met
290                 295                 300                 305 ggc gac aac tgg gac atg atg tac gtg ggt atg tac cag gat atc aac     1019
Gly Asp Asn Trp Asp Met Met Tyr Val Gly Met Tyr Gln Asp Ile Asn
                 310                 315                 320 tgg gat aac gac aac ggc acc aag tgg tgg acc gtc ggt att cgc ccg     1067
```

```
Trp Asp Asn Asp Asn Gly Thr Lys Trp Trp Thr Val Gly Ile Arg Pro
            325                 330                 335 atg tac aag tgg acg cca atc atg agc acc gtg atg gaa atc ggc tac      1115
Met Tyr Lys Trp Thr Pro Ile Met Ser Thr Val Met Glu Ile Gly Tyr
            340                 345                 350 gac aac gtc gaa tcc cag cgc acc ggc gac aag aac aat cag tac aaa      1163
Asp Asn Val Glu Ser Gln Arg Thr Gly Asp Lys Asn Asn Gln Tyr Lys
            355                 360                 365 att acc ctc gca caa caa tgg cag gct ggc gac agc atc tgg tca cgc      1211
Ile Thr Leu Ala Gln Gln Trp Gln Ala Gly Asp Ser Ile Trp Ser Arg
370                 375                 380                 385 ccg gct att cgt gtc ttc gca acc tac gcc aag tgg gat gag aaa tgg      1259
Pro Ala Ile Arg Val Phe Ala Thr Tyr Ala Lys Trp Asp Glu Lys Trp
                390                 395                 400 ggt tac gac tac acc ggt aac gct gat aac aac gcg aac ttc ggc aaa      1307
Gly Tyr Asp Tyr Thr Gly Asn Ala Asp Asn Asn Ala Asn Phe Gly Lys
                405                 410                 415 gcc gtt cct gct gat ttc aac ggc ggc agc ttc ggt cgt ggc gac agc      1355
Ala Val Pro Ala Asp Phe Asn Gly Gly Ser Phe Gly Arg Gly Asp Ser
                420                 425                 430 gac gag tgg acc ttc ggt gcc cag atg gaa atc tgg tgg taa              1397
Asp Glu Trp Thr Phe Gly Ala Gln Met Glu Ile Trp Trp
            435                 440                 445 tagcaaaacc tgggccggat aaggcgttta cgccgcattc ggcaaccaac gcctgatgcg    1457
acgcttgcgc gtcttatcag gcctacaacg gctgtaagct t                       1498

<210> SEQ ID NO 4
<211> LENGTH: 446
<212> TYPE: PRT
<213> ORGANISM: Escherichia coli

<400> SEQUENCE: 4

Met Met Ile Thr Leu Arg Lys Leu Pro Leu Ala Val Ala Val Ala Ala
1               5                   10                  15

Gly Val Met Ser Ala Gln Ala Met Ala Val Asp Phe His Gly Tyr Ala
            20                  25                  30

Arg Ser Gly Ile Gly Trp Thr Gly Ser Gly Gly Glu Gln Gln Cys Phe
        35                  40                  45

Gln Thr Thr Gly Ala Gln Ser Lys Ser Tyr Arg Leu Gly Asn Glu Cys Glu
    50                  55                  60

Thr Tyr Ala Glu Leu Lys Leu Gly Gln Glu Val Trp Lys Glu Gly Asp
65                  70                  75                  80

Lys Ser Phe Tyr Phe Asp Thr Asn Val Ala Tyr Ser Val Ala Gln Gln
                85                  90                  95

Asn Asp Trp Glu Ala Thr Asp Pro Ala Phe Arg Glu Ala Asn Val Gln
            100                 105                 110

Gly Lys Asn Leu Ile Glu Trp Leu Pro Gly Ser Thr Ile Trp Ala Gly
        115                 120                 125

Lys Arg Phe Tyr Gln Arg His Asp Val His Met Ile Asp Phe Tyr Tyr
    130                 135                 140

Trp Asp Ile Ser Gly Pro Gly Ala Gly Leu Glu Asn Ile Asp Val Gly
145                 150                 155                 160

Phe Gly Lys Leu Ser Leu Ala Ala Thr Arg Ser Ser Glu Ala Gly Gly
                165                 170                 175

Ser Ser Ser Phe Ala Ser Asn Asn Ile Tyr Asp Tyr Thr Asn Glu Thr
            180                 185                 190
```

```
Ala Asn Asp Val Phe Asp Val Arg Leu Ala Gln Met Glu Ile Asn Pro
        195                 200                 205
Gly Gly Thr Leu Glu Leu Gly Val Asp Tyr Gly Arg Ala Asn Leu Arg
    210                 215                 220
Asp Asn Tyr Arg Leu Val Asp Gly Ala Ser Lys Asp Gly Trp Leu Phe
225                 230                 235                 240
Thr Ala Glu His Thr Gln Ser Val Leu Lys Gly Phe Asn Lys Phe Val
                245                 250                 255
Val Gln Tyr Ala Thr Asp Ser Met Thr Ser Gln Gly Lys Gly Leu Ser
            260                 265                 270
Gln Gly Ser Gly Val Ala Phe Asp Asn Glu Lys Phe Ala Tyr Asn Ile
        275                 280                 285
Asn Asn Asn Gly His Met Leu Arg Ile Leu Asp His Gly Ala Ile Ser
    290                 295                 300
Met Gly Asp Asn Trp Asp Met Met Tyr Val Gly Met Tyr Gln Asp Ile
305                 310                 315                 320
Asn Trp Asp Asn Asp Asn Gly Thr Lys Trp Trp Thr Val Gly Ile Arg
                325                 330                 335
Pro Met Tyr Lys Trp Thr Pro Ile Met Ser Thr Val Met Glu Ile Gly
            340                 345                 350
Tyr Asp Asn Val Glu Ser Gln Arg Thr Gly Asp Lys Asn Asn Gln Tyr
        355                 360                 365
Lys Ile Thr Leu Ala Gln Gln Trp Gln Ala Gly Asp Ser Ile Trp Ser
    370                 375                 380
Arg Pro Ala Ile Arg Val Phe Ala Thr Tyr Ala Lys Trp Asp Glu Lys
385                 390                 395                 400
Trp Gly Tyr Asp Tyr Thr Gly Asn Ala Asp Asn Asn Ala Asn Phe Gly
                405                 410                 415
Lys Ala Val Pro Ala Asp Phe Asn Gly Gly Ser Phe Gly Arg Gly Asp
            420                 425                 430
Ser Asp Glu Trp Thr Phe Gly Ala Gln Met Glu Ile Trp Trp
        435                 440                 445

<210> SEQ ID NO 5
<211> LENGTH: 1341
<212> TYPE: DNA
<213> ORGANISM: Shigella flexneri
<220> FEATURE:
<221> NAME/KEY: CDS
<222> LOCATION: (1)..(1341)
<223> OTHER INFORMATION: lamB coding region

<400> SEQUENCE: 5 atg atg att act ctg cgc aaa ctt cct ctg gcg gtt gcc gtc gca gcg      48
Met Met Ile Thr Leu Arg Lys Leu Pro Leu Ala Val Ala Val Ala Ala
1               5                   10                  15 ggc gta atg tct gct cag gca atg gct gtt gat ttc cac ggc tat gca     96
Gly Val Met Ser Ala Gln Ala Met Ala Val Asp Phe His Gly Tyr Ala
            20                  25                  30 cgt tcc ggt att ggc tgg aca ggt agc ggc ggt gaa caa cag tgt ttc    144
Arg Ser Gly Ile Gly Trp Thr Gly Ser Gly Gly Glu Gln Gln Cys Phe
        35                  40                  45 cag act acc ggt gct caa agt aaa tac cgt ctt ggc aac gaa tgt gaa    192
Gln Thr Thr Gly Ala Gln Ser Lys Tyr Arg Leu Gly Asn Glu Cys Glu
    50                  55                  60 act tat gct gaa tta aaa ttg ggt cag gaa gtg tgg aaa gag ggc gat    240
Thr Tyr Ala Glu Leu Lys Leu Gly Gln Glu Val Trp Lys Glu Gly Asp
65                  70                  75                  80
```

-continued

```
aag agc ttc tat ttc gac act aac gtg gcc tat tcc gtc gcg caa cag        288
Lys Ser Phe Tyr Phe Asp Thr Asn Val Ala Tyr Ser Val Ala Gln Gln
            85                  90                  95 aat gac tgg gaa gct acc gat ccg gcc ttc cgt gaa gca aac gtg cag        336
Asn Asp Trp Glu Ala Thr Asp Pro Ala Phe Arg Glu Ala Asn Val Gln
        100                 105                 110 gga aaa aac ctg atc gaa tgg ctg cca ggt tcc acc atc tgg gca ggt        384
Gly Lys Asn Leu Ile Glu Trp Leu Pro Gly Ser Thr Ile Trp Ala Gly
    115                 120                 125 aag cgc ttc tac caa cgt cat gac gtt cat atg atc gac ttc tac tac        432
Lys Arg Phe Tyr Gln Arg His Asp Val His Met Ile Asp Phe Tyr Tyr
130                 135                 140 tgg gat att tct ggt cct ggt gcc ggt ctg gaa aac atc gat gtt ggc        480
Trp Asp Ile Ser Gly Pro Gly Ala Gly Leu Glu Asn Ile Asp Val Gly
145                 150                 155                 160 ttc ggt aaa ctc tct ctg gca gca acc cgc tcc tct gaa gct ggt ggt        528
Phe Gly Lys Leu Ser Leu Ala Ala Thr Arg Ser Ser Glu Ala Gly Gly
                165                 170                 175 tct tcc tct ttt gcc agc aac aat att tat gac tat acc aac gaa acc        576
Ser Ser Ser Phe Ala Ser Asn Asn Ile Tyr Asp Tyr Thr Asn Glu Thr
            180                 185                 190 gcg aac gac gtt ttc gat gtg cgt tta gcg cag atg gaa atc aac ccg        624
Ala Asn Asp Val Phe Asp Val Arg Leu Ala Gln Met Glu Ile Asn Pro
        195                 200                 205 ggc ggc aca tta gaa ctg ggt gtc gac tac ggt cgt gcc aac ctg cgt        672
Gly Gly Thr Leu Glu Leu Gly Val Asp Tyr Gly Arg Ala Asn Leu Arg
    210                 215                 220 gat aac tat cgt ctg gtt gat ggc gca tcg aaa gac ggc tgg tta ttc        720
Asp Asn Tyr Arg Leu Val Asp Gly Ala Ser Lys Asp Gly Trp Leu Phe
225                 230                 235                 240 act gct gaa cat act cag agt gtc ctg aag ggc ttt aac aag ttt gtt        768
Thr Ala Glu His Thr Gln Ser Val Leu Lys Gly Phe Asn Lys Phe Val
                245                 250                 255 gtt cag tac gct act gac tcg atg acc tcg cag ggt aaa ggt ctg tcg        816
Val Gln Tyr Ala Thr Asp Ser Met Thr Ser Gln Gly Lys Gly Leu Ser
            260                 265                 270 cag ggt tct ggc gtc gcg ttt gat aac gaa aaa ttt gcc tac aat atc        864
Gln Gly Ser Gly Val Ala Phe Asp Asn Glu Lys Phe Ala Tyr Asn Ile
        275                 280                 285 aac aac aac ggt cac atg ctg cgt atc ctc gac cac ggt gcg atc tcc        912
Asn Asn Asn Gly His Met Leu Arg Ile Leu Asp His Gly Ala Ile Ser
    290                 295                 300 atg ggc gac aac tgg gac atg atg tac gtg ggt atg tac cag gat atc        960
Met Gly Asp Asn Trp Asp Met Met Tyr Val Gly Met Tyr Gln Asp Ile
305                 310                 315                 320 aac tgg gat aac gac aac ggc acc aag tgg tgg acc gtt ggt att cgc       1008
Asn Trp Asp Asn Asp Asn Gly Thr Lys Trp Trp Thr Val Gly Ile Arg
                325                 330                 335 ccg atg tac aag tgg acg cca atc atg agc acc gtg atg gaa atc ggc       1056
Pro Met Tyr Lys Trp Thr Pro Ile Met Ser Thr Val Met Glu Ile Gly
            340                 345                 350 tac gac aac gtc gaa tcc cag cgc acc ggc gac aag aac aat cag tac       1104
Tyr Asp Asn Val Glu Ser Gln Arg Thr Gly Asp Lys Asn Asn Gln Tyr
        355                 360                 365 aaa att acc ctc gca caa caa tgg cag gct ggc gac agc atc tgg tca       1152
Lys Ile Thr Leu Ala Gln Gln Trp Gln Ala Gly Asp Ser Ile Trp Ser
    370                 375                 380 cgc ccg gct att cgt gtc ttc gca acc tac gcc aag tgg gat gag aaa       1200
Arg Pro Ala Ile Arg Val Phe Ala Thr Tyr Ala Lys Trp Asp Glu Lys
```

```
                385               390               395               400
tgg ggt tac gac tac aac ggc gat agc aag gtt aac ccg aac tac ggc     1248
Trp Gly Tyr Asp Tyr Asn Gly Asp Ser Lys Val Asn Pro Asn Tyr Gly
                405               410               415 aaa gcc gtt cct gct gat ttc aac ggc agc ttc ggt cgt ggc gac         1296
Lys Ala Val Pro Ala Asp Phe Asn Gly Gly Ser Phe Gly Arg Gly Asp
            420               425               430 agc gac gag tgg acc ttc ggt gcc cag atg gaa atc tgg tgg taa         1341
Ser Asp Glu Trp Thr Phe Gly Ala Gln Met Glu Ile Trp Trp
            435               440               445

<210> SEQ ID NO 6
<211> LENGTH: 446
<212> TYPE: PRT
<213> ORGANISM: Shigella flexneri

<400> SEQUENCE: 6

Met Met Ile Thr Leu Arg Lys Leu Pro Leu Ala Val Ala Val Ala Ala
1               5                   10                  15

Gly Val Met Ser Ala Gln Ala Met Ala Val Asp Phe His Gly Tyr Ala
                20                  25                  30

Arg Ser Gly Ile Gly Trp Thr Gly Ser Gly Gly Glu Gln Gln Cys Phe
            35                  40                  45

Gln Thr Thr Gly Ala Gln Ser Lys Tyr Arg Leu Gly Asn Glu Cys Glu
        50                  55                  60

Thr Tyr Ala Glu Leu Lys Leu Gly Gln Glu Val Trp Lys Glu Gly Asp
65                  70                  75                  80

Lys Ser Phe Tyr Phe Asp Thr Asn Val Ala Tyr Ser Val Ala Gln Gln
                85                  90                  95

Asn Asp Trp Glu Ala Thr Asp Pro Ala Phe Arg Glu Ala Asn Val Gln
            100                 105                 110

Gly Lys Asn Leu Ile Glu Trp Leu Pro Gly Ser Thr Ile Trp Ala Gly
        115                 120                 125

Lys Arg Phe Tyr Gln Arg His Asp Val His Met Ile Asp Phe Tyr Tyr
    130                 135                 140

Trp Asp Ile Ser Gly Pro Gly Ala Gly Leu Glu Asn Ile Asp Val Gly
145                 150                 155                 160

Phe Gly Lys Leu Ser Leu Ala Ala Thr Arg Ser Ser Glu Ala Gly Gly
                165                 170                 175

Ser Ser Ser Phe Ala Ser Asn Asn Ile Tyr Asp Tyr Thr Asn Glu Thr
            180                 185                 190

Ala Asn Asp Val Phe Asp Val Arg Leu Ala Gln Met Glu Ile Asn Pro
        195                 200                 205

Gly Gly Thr Leu Glu Leu Gly Val Asp Tyr Gly Arg Ala Asn Leu Arg
    210                 215                 220

Asp Asn Tyr Arg Leu Val Asp Gly Ala Ser Lys Asp Gly Trp Leu Phe
225                 230                 235                 240

Thr Ala Glu His Thr Gln Ser Val Leu Lys Gly Phe Asn Lys Phe Val
                245                 250                 255

Val Gln Tyr Ala Thr Asp Ser Met Thr Ser Gln Gly Lys Gly Leu Ser
            260                 265                 270

Gln Gly Ser Gly Val Ala Phe Asp Asn Glu Lys Phe Ala Tyr Asn Ile
        275                 280                 285

Asn Asn Asn Gly His Met Leu Arg Ile Leu Asp His Gly Ala Ile Ser
    290                 295                 300
```

```
Met Gly Asp Asn Trp Asp Met Met Tyr Val Gly Met Tyr Gln Asp Ile
305                 310                 315                 320

Asn Trp Asp Asn Asp Asn Gly Thr Lys Trp Thr Val Gly Ile Arg
            325                 330                 335

Pro Met Tyr Lys Trp Thr Pro Ile Met Ser Thr Val Met Glu Ile Gly
            340                 345                 350

Tyr Asp Asn Val Glu Ser Gln Arg Thr Gly Asp Lys Asn Asn Gln Tyr
            355                 360                 365

Lys Ile Thr Leu Ala Gln Gln Trp Gln Ala Gly Asp Ser Ile Trp Ser
            370                 375                 380

Arg Pro Ala Ile Arg Val Phe Ala Thr Tyr Ala Lys Trp Asp Glu Lys
385                 390                 395                 400

Trp Gly Tyr Asp Tyr Asn Gly Asp Ser Lys Val Asn Pro Asn Tyr Gly
                405                 410                 415

Lys Ala Val Pro Ala Asp Phe Asn Gly Gly Ser Phe Gly Arg Gly Asp
                420                 425                 430

Ser Asp Glu Trp Thr Phe Gly Ala Gln Met Glu Ile Trp Trp
            435                 440                 445

<210> SEQ ID NO 7
<211> LENGTH: 1359
<212> TYPE: DNA
<213> ORGANISM: Salmonella typhimurium
<220> FEATURE:
<221> NAME/KEY: CDS
<222> LOCATION: (1)..(1359)
<223> OTHER INFORMATION: lamB coding region

<400> SEQUENCE: 7 atg atg att act ctg cgc aaa ctc cca ctg gcg gtt gct gtc gca gcg      48
Met Met Ile Thr Leu Arg Lys Leu Pro Leu Ala Val Ala Val Ala Ala
1               5                   10                  15 ggc gta atg tcc gct cag gca atg gct gtc gat ttc cac ggt tac gcc      96
Gly Val Met Ser Ala Gln Ala Met Ala Val Asp Phe His Gly Tyr Ala
                20                  25                  30 cgt tcc ggt att ggc tgg acg gga agc ggc ggc gaa caa cag tgt ttc     144
Arg Ser Gly Ile Gly Trp Thr Gly Ser Gly Gly Glu Gln Gln Cys Phe
            35                  40                  45 cag gca acg ggt gcc caa agt aaa tac cgt ctc ggt aac gaa tgt gaa     192
Gln Ala Thr Gly Ala Gln Ser Lys Tyr Arg Leu Gly Asn Glu Cys Glu
50                  55                  60 acc tat gcg gaa ctg aaa ctg ggc cag gaa gtg tgg aaa gag ggc gat     240
Thr Tyr Ala Glu Leu Lys Leu Gly Gln Glu Val Trp Lys Glu Gly Asp
65                  70                  75                  80 aag agc ttc tat ttc gac acc aac gtc gcc tat tcg gtt aac cag cag     288
Lys Ser Phe Tyr Phe Asp Thr Asn Val Ala Tyr Ser Val Asn Gln Gln
                85                  90                  95 aac gac tgg gaa tcg acc gat ccc gcc ttc cgc gaa gcg aac gtg cag     336
Asn Asp Trp Glu Ser Thr Asp Pro Ala Phe Arg Glu Ala Asn Val Gln
            100                 105                 110 ggt aaa aac ctg att gaa tgg ctg ccg ggc tct acc atc tgg gcc ggt     384
Gly Lys Asn Leu Ile Glu Trp Leu Pro Gly Ser Thr Ile Trp Ala Gly
        115                 120                 125 aag cgc ttc tat cag cgt cat gac gta cac atg atc gac ttc tac tac     432
Lys Arg Phe Tyr Gln Arg His Asp Val His Met Ile Asp Phe Tyr Tyr
    130                 135                 140 tgg gat att tca ggt cct ggc gca ggt atc gaa aat atc gat ctg ggc     480
Trp Asp Ile Ser Gly Pro Gly Ala Gly Ile Glu Asn Ile Asp Leu Gly
145                 150                 155                 160
```

```
ttc ggt aag ctt tca ctg gcg gcg acc cgg tct act gaa gcg ggc ggc      528
Phe Gly Lys Leu Ser Leu Ala Ala Thr Arg Ser Thr Glu Ala Gly Gly
            165                 170                 175 tct tac acc ttc agc agc cag aat att tat gat gaa gtg aaa gat acc      576
Ser Tyr Thr Phe Ser Ser Gln Asn Ile Tyr Asp Glu Val Lys Asp Thr
                180                 185                 190 gct aac gac gtc ttt gac gta cgt ctg gct ggt ctg caa acg aac ccg      624
Ala Asn Asp Val Phe Asp Val Arg Leu Ala Gly Leu Gln Thr Asn Pro
            195                 200                 205 gac ggc gta ctg gag cta ggc gtt gat tac ggt cgc gcc aat acg acc      672
Asp Gly Val Leu Glu Leu Gly Val Asp Tyr Gly Arg Ala Asn Thr Thr
        210                 215                 220 gat ggt tat aag ctg gct gat ggg gca tcg aaa gac ggc tgg atg ttc      720
Asp Gly Tyr Lys Leu Ala Asp Gly Ala Ser Lys Asp Gly Trp Met Phe
225                 230                 235                 240 acc gcc gaa cac acg caa agc atg ttg aaa ggc tat aac aag ttt gtc      768
Thr Ala Glu His Thr Gln Ser Met Leu Lys Gly Tyr Asn Lys Phe Val
                245                 250                 255 gtg caa tat gcc acc gat gcc atg acc acg cag ggt aaa ggc cag gcg      816
Val Gln Tyr Ala Thr Asp Ala Met Thr Thr Gln Gly Lys Gly Gln Ala
            260                 265                 270 cgc ggt tcc gac ggt tct tca tct ttc act gaa gaa ttg tct gat gga      864
Arg Gly Ser Asp Gly Ser Ser Ser Phe Thr Glu Glu Leu Ser Asp Gly
        275                 280                 285 acc aaa att aat tac gcc aat aag gtc atc aat aat aat ggc aat atg      912
Thr Lys Ile Asn Tyr Ala Asn Lys Val Ile Asn Asn Asn Gly Asn Met
    290                 295                 300 tgg cgt att ttg gat cat ggc gcc atc tcg ctt ggt gat aaa tgg gat      960
Trp Arg Ile Leu Asp His Gly Ala Ile Ser Leu Gly Asp Lys Trp Asp
305                 310                 315                 320 ttg atg tac gtc ggt atg tac cag aat atc gat tgg gat aat aac ctg     1008
Leu Met Tyr Val Gly Met Tyr Gln Asn Ile Asp Trp Asp Asn Asn Leu
                325                 330                 335 ggt act gag tgg tgg acc gtg ggt gta cgt cca atg tac aag tgg acg     1056
Gly Thr Glu Trp Trp Thr Val Gly Val Arg Pro Met Tyr Lys Trp Thr
            340                 345                 350 cca atc atg agc acc ctg ctg gaa gtc ggc tac gac aac gtg aaa tct     1104
Pro Ile Met Ser Thr Leu Leu Glu Val Gly Tyr Asp Asn Val Lys Ser
        355                 360                 365 cag cag acc ggc gat cgt aac aat caa tat aaa atc acc ctg gcg caa     1152
Gln Gln Thr Gly Asp Arg Asn Asn Gln Tyr Lys Ile Thr Leu Ala Gln
    370                 375                 380 cag tgg cag gcg ggc gac agc atc tgg tcg cgt ccg gct atc cgt att     1200
Gln Trp Gln Ala Gly Asp Ser Ile Trp Ser Arg Pro Ala Ile Arg Ile
385                 390                 395                 400 ttc gcc acc tac gcg aaa tgg gat gag aaa tgg ggc tat atc aaa gac     1248
Phe Ala Thr Tyr Ala Lys Trp Asp Glu Lys Trp Gly Tyr Ile Lys Asp
                405                 410                 415 ggc gat aac att tcc cgt tat gcc gca gcg act aac tcc ggc att tcc     1296
Gly Asp Asn Ile Ser Arg Tyr Ala Ala Ala Thr Asn Ser Gly Ile Ser
            420                 425                 430 acc aac agc cgt ggc gat agc gat gag tgg acc ttc ggc gcc cag atg     1344
Thr Asn Ser Arg Gly Asp Ser Asp Glu Trp Thr Phe Gly Ala Gln Met
        435                 440                 445 gaa atc tgg tgg taa                                                  1359
Glu Ile Trp Trp
    450

<210> SEQ ID NO 8
<211> LENGTH: 452
```

<212> TYPE: PRT
<213> ORGANISM: Salmonella typhimurium

<400> SEQUENCE: 8

```
Met Met Ile Thr Leu Arg Lys Leu Pro Leu Ala Val Ala Val Ala Ala
1               5                   10                  15

Gly Val Met Ser Ala Gln Ala Met Ala Val Asp Phe His Gly Tyr Ala
            20                  25                  30

Arg Ser Gly Ile Gly Trp Thr Gly Ser Gly Glu Gln Gln Cys Phe
        35                  40                  45

Gln Ala Thr Gly Ala Gln Ser Lys Tyr Arg Leu Gly Asn Glu Cys Glu
50                  55                  60

Thr Tyr Ala Glu Leu Lys Leu Gly Gln Glu Val Trp Lys Glu Gly Asp
65                  70                  75                  80

Lys Ser Phe Tyr Phe Asp Thr Asn Val Ala Tyr Ser Val Asn Gln Gln
                85                  90                  95

Asn Asp Trp Glu Ser Thr Asp Pro Ala Phe Arg Glu Ala Asn Val Gln
            100                 105                 110

Gly Lys Asn Leu Ile Glu Trp Leu Pro Gly Ser Thr Ile Trp Ala Gly
        115                 120                 125

Lys Arg Phe Tyr Gln Arg His Asp Val His Met Ile Asp Phe Tyr Tyr
130                 135                 140

Trp Asp Ile Ser Gly Pro Gly Ala Gly Ile Glu Asn Ile Asp Leu Gly
145                 150                 155                 160

Phe Gly Lys Leu Ser Leu Ala Ala Thr Arg Ser Thr Glu Ala Gly Gly
                165                 170                 175

Ser Tyr Thr Phe Ser Ser Gln Asn Ile Tyr Asp Glu Val Lys Asp Thr
            180                 185                 190

Ala Asn Asp Val Phe Asp Val Arg Leu Ala Gly Leu Gln Thr Asn Pro
        195                 200                 205

Asp Gly Val Leu Glu Leu Gly Val Asp Tyr Gly Arg Ala Asn Thr Thr
210                 215                 220

Asp Gly Tyr Lys Leu Ala Asp Gly Ala Ser Lys Asp Gly Trp Met Phe
225                 230                 235                 240

Thr Ala Glu His Thr Gln Ser Met Leu Lys Gly Tyr Asn Lys Phe Val
                245                 250                 255

Val Gln Tyr Ala Thr Asp Ala Met Thr Thr Gln Gly Lys Gly Gln Ala
            260                 265                 270

Arg Gly Ser Asp Gly Ser Ser Phe Thr Glu Glu Leu Ser Asp Gly
        275                 280                 285

Thr Lys Ile Asn Tyr Ala Asn Lys Val Ile Asn Asn Gly Asn Met
290                 295                 300

Trp Arg Ile Leu Asp His Gly Ala Ile Ser Leu Gly Asp Lys Trp Asp
305                 310                 315                 320

Leu Met Tyr Val Gly Met Tyr Gln Asn Ile Asp Trp Asp Asn Asn Leu
                325                 330                 335

Gly Thr Glu Trp Trp Thr Val Gly Val Arg Pro Met Tyr Lys Trp Thr
            340                 345                 350

Pro Ile Met Ser Thr Leu Leu Glu Val Gly Tyr Asp Asn Val Lys Ser
        355                 360                 365

Gln Gln Thr Gly Asp Arg Asn Asn Gln Tyr Lys Ile Thr Leu Ala Gln
370                 375                 380

Gln Trp Gln Ala Gly Asp Ser Ile Trp Ser Arg Pro Ala Ile Arg Ile
385                 390                 395                 400
```

```
Phe Ala Thr Tyr Ala Lys Trp Asp Glu Lys Trp Gly Tyr Ile Lys Asp
                405                 410                 415

Gly Asp Asn Ile Ser Arg Tyr Ala Ala Ala Thr Asn Ser Gly Ile Ser
            420                 425                 430

Thr Asn Ser Arg Gly Asp Ser Asp Glu Trp Thr Phe Gly Ala Gln Met
        435                 440                 445

Glu Ile Trp Trp
    450
```